(12) United States Patent
Egelberg et al.

(10) Patent No.: US 9,423,342 B2
(45) Date of Patent: Aug. 23, 2016

(54) DETERMINATION OF PHYSICAL PARAMETERS ASSOCIATED WITH ERYTHROCYTES

(75) Inventors: Peter Egelberg, Lund (SE); Mikael Sebesta, Dalby (SE); Anders Isaksson, Staffenstorp (SE)

(73) Assignee: Phase Holographic Imaging PHI AB, Lund (SE)

( * ) Notice: Subject to any disclaimer, the term of this patent is extended or adjusted under 35 U.S.C. 154(b) by 57 days.

(21) Appl. No.: 13/982,951

(22) PCT Filed: Feb. 15, 2012

(86) PCT No.: PCT/SE2012/050161
§ 371 (c)(1),
(2), (4) Date: Jan. 6, 2014

(87) PCT Pub. No.: WO2012/112114
PCT Pub. Date: Aug. 23, 2012

(65) Prior Publication Data
US 2014/0113323 A1  Apr. 24, 2014

Related U.S. Application Data

(60) Provisional application No. 61/443,487, filed on Feb. 16, 2011.

(30) Foreign Application Priority Data

Feb. 16, 2011 (SE) ..................................... 1150125

(51) Int. Cl.
*G01B 9/021* (2006.01)
*G01N 21/41* (2006.01)
(Continued)

(52) U.S. Cl.
CPC .............. *G01N 21/41* (2013.01); *G01N 21/453* (2013.01); *G03H 1/0866* (2013.01); *G03H 2001/0447* (2013.01)

(58) Field of Classification Search
CPC ...... G01N 21/41; G01N 21/453; G01N 21/17; G01N 21/45; G01N 21/455; G03H 1/0866; G03H 2001/0447; G03H 2001/02083; G03H 2001/021; G01J 9/00; G01J 9/02; G01J 2009/00; G01J 2009/02; G01J 2009/002

USPC ......................................................... 356/457
See application file for complete search history.

(56) References Cited

U.S. PATENT DOCUMENTS 6,262,818 B1   7/2001   Cuche et al.
7,649,160 B2   1/2010   Colomb et al.
(Continued)

FOREIGN PATENT DOCUMENTS

CN   101346673 A   1/2009
JP   2005-114678 A   4/2005
(Continued)

OTHER PUBLICATIONS

Rappaz et al., Comparative Study of Human Erythrocytes by Digital Holographic Microscopy, Confocal Microscopy, and Impedance Volume Analyzer, Cytometry Part A, vol. 73, NR 10, pp. 895-903, 2008, ISSN 1552-4930 (Electronic).
(Continued)

*Primary Examiner* — Tarifur Chowdhury
*Assistant Examiner* — Jonathon Cook
(74) *Attorney, Agent, or Firm* — Harness, Dickey & Pierce, P.L.C.

(57) ABSTRACT

A method based on digital holography for determining parameters of at least one erythrocyte is provided, said method comprising the steps of: constructing an interference pattern comprising a wave front representative of said at least one erythrocyte arised from the interaction of said at least one erythrocyte and electromagnetic radiation, reconstructing amplitude-and phase information representative of said at least one erythrocyte wave front from said interference pattern and determining the mean corpuscular volume and/or mean corpuscular hemoglobin concentration and/or oxygen saturation and/or mean corpuscular hemoglobin of at least one erythrocyte by combining phase information and amplitude information representative of said at least one erythrocyte.

17 Claims, 4 Drawing Sheets

(51) Int. Cl.
  *G03H 1/08*    (2006.01)
  *G01N 21/45*   (2006.01)
  *G03H 1/04*    (2006.01)

(56) References Cited

U.S. PATENT DOCUMENTS

2003/0033102 A1* 2/2003 Dietiker .................. 702/85
2008/0265130 A1  10/2008 Colomb et al.

FOREIGN PATENT DOCUMENTS

| JP | 2009-521216 A   | 6/2009 |
| WO | WO-0020929 A1   | 4/2000 |
| WO | WO-2006090320 A1 | 8/2006 |
| WO | WO-2007073345 A1 | 6/2007 |

OTHER PUBLICATIONS

Cuche et al., Simultaneous Amplitude-Contrast and Quantitative Phase-Contrast Microscopy by Numerical Reconstruction of Fresnel Off-Axis Holograms, Applied Optics, Dec. 1, 1999, Opt. Soc. America, USA, ISSN 0003-6935 (print), vol. 38, Nr. 34, pp. 6994-7001.

Rappaz et al., Measurement of the Integral Refractive Index and Dynamic Cell Morphometry of Living Cells With Digital Holographic Microscopy., Optics Express, vol. 13, No. 23, pp. 936-9373, 2005.

International Search Report PCT/ISA/210 for International Application No. PCT/SE2012/050161 Dated on Feb. 15, 2012.

English translation of Notice of Reasons for Rejection for JP Application No. 2013-554419 dated Jan. 5, 2016.

Chinese Office Action for CN Application No. 201280007685.1 dated Sep. 11, 2015.

* cited by examiner

DETERMINATION OF PHYSICAL PARAMETERS ASSOCIATED WITH ERYTHROCYTES

This application is the national phase under 35 U.S.C. §371 of PCT International Application No. PCT/SE2012/050161 which has an International filing date of Feb. 15, 2012, and which claims priority to Sweden patent application number SESN 1150125-1 filed Feb. 16, 2011 and also to U.S. Ser. No. 61/443,487.

TECHNICAL FIELD OF THE INVENTION

The present invention relates to a method and apparatus based on digital holography to determine physical parameters associated with erythrocytes.

TECHNICAL BACKGROUND

For diagnostic purposes, a commonly used tool is a complete blood count (CBC). The CBC can be divided into three important types of cells that are used for analysis. It is the white blood cells (leukocytes), red blood cells (erythrocytes), and platelets (thrombocytes). By determining important features of erythrocytes, such as mean corpuscular volume (MCV)—the average volume of the erythrocyte, red blood cell distribution width (RDW)—a measure of the variation of the red blood cell population, mean corpuscular hemoglobin (MCH)—the average amount of hemoglobin per erythrocyte, oxygen saturation ($S_{O2}$)—a measure of the percentage of hemoglobin binding sites in the erythrocyte occupied by oxygen and mean corpuscular hemoglobin concentration (MCHC)—the average concentration of hemoglobin in the erythrocyte, it is possible to diagnose a variety of diseases. For instance is anemia classified as microcytic or macrocytic based on whether the MCV value, is above or below the expected normal range. At present these parameters can be measured by complex and expensive systems, e.g. flow-cytometers and confocal laser scanning microscopy, or systems only capable of only measuring one parameter, e.g. impedance volume analyzer instruments.

In the article "Comparative Study of Human Erythrocytes by Digital Holographic Microscopy, Confocal Microscopy, and Impedance Volume Analyzer" by Rappaz et al. (Journal of the International Society for Advancement of Cytometry, 73A:895-903, 2008), a technique is described that demonstrates the applicability of the digital holography microscopy technique, in combination with a decoupling procedure, for the measurements of refractive indices and volumes of intact individual erythrocytes. Further the decoupling procedure is explained in greater detail in the article "Measurement of the integral refractive index and dynamic cell morphometry of living cells with digital holographic microscopy" by Rappaz et al. (OPTICS EXPRESS, Vol. 13, No. 23, 936-9373, 2005), where an experimental protocol called "decoupling procedure" is presented with the aim of measuring separately the integral refractive index and the cellular thickness from the quantitative phase images of living cells.

Thus, in order to calculate erythrocyte parameters such as MCV and/or MCHC and/or RDW and/or $S_{O2}$ and/or MCH it is necessary to have the erythrocyte(s) in a solution and perform an exchange of said solution to a second solution, where the refractive index of the two solutions must be known. This is a laborious and time consuming approach where it requires substantial laboratory skills in performing this without for example contaminating the erythrocytes. Further, the process of exchanging solutions is an additional step that increases the risk of a mishap in the measurement by user interaction. An additional draw back when exchanging solutions, is the fact that all the erythrocytes present in the sample with the first solution will probably not be present after the washing out of the first solution and replacement with the second solution, meaning that there will be a loss, or contamination, of the sample. This reduction of erythrocytes in the solution exchange process, are attributed to that it is necessary to allow the erythrocytes to settle and adhere to the observation vessel before doing the first measurement. If the erythrocytes do not adhere properly, they will unbind and wash out with the first solution and/or move to a new position and adhere on the observation vessel. This will consequently affect the quality of the reconstructed wave front of the erythrocytes by introducing artifacts. Further, the exchange and presence of fluids could affect the erythrocytes morphology and/or desired behavior in an unwanted way. The observation vessel must also only be used one time, so not to contaminate the measurement by for example diluting and/or mixing the solutions and thereby influencing the refractive index to become an unknown instead of as assumed known factor. Further, producing observation vessels with a specific height is very difficult with one time consumables with the required accuracy in the nm range.

Hence, an improved method of determining said parameters is advantageous, and in particular a faster, easier and more reliable method is desired.

SUMMARY OF THE INVENTION

Accordingly, the invention seeks to mitigate, alleviate or eliminate one or more of the above mentioned disadvantages singly or in any combination. In particular, it may be seen as an object of the present invention to determine the mean corpuscular volume, red blood cell distribution width, mean corpuscular hemoglobin, oxygen saturation and mean corpuscular hemoglobin concentration of an erythrocyte without the need of exchanging- and/or the existence of solutions.

According to a first aspect, the above and further objects are solved by a method based on digital holography for determining parameters of at least one erythrocyte, comprising the steps of:
constructing an interference pattern comprising a wave front representative of said at least one erythrocyte arised from the interaction of said at least one erythrocyte and electromagnetic radiation;
reconstructing amplitude- and phase information representative of said at least one erythrocyte wave front from said interference pattern; and
determining the mean corpuscular volume and/or mean corpuscular hemoglobin concentration and/or oxygen saturation and/or mean corpuscular hemoglobin of at least one erythrocyte by combining phase information and amplitude information representative of said at least one erythrocyte.

In the article "Comparative Study of Human Erythrocytes by Digital Holographic Microscopy, Confocal Microscopy, and Impedance Volume Analyzer" there is disclosed a method were the amplitude information is not involved or used in the method. The suggested method in the article of Rappaz et al. involves using two different images, taken when different sample fluids are used and using the difference of these images to be able to determine the mean corpuscular volume and mean corpuscular hemoglobin. The present invention, however, is directed to a method were the amplitude information is used in combination with the phase information, which creates the basis for determining the parameters from only one image, i.e. without for instance the use of different cell fluids. This and further advantages of the present invention are further disclosed below.

By the method of the present invention, oxygen saturation is determined by use of reconstructed amplitude- and/or phase information at two or more wavelengths.

The method of the present invention enables the determination of the mean corpuscular volume, red blood cell distribution width, mean corpuscular hemoglobin, oxygen saturation and mean corpuscular hemoglobin concentration of an erythrocyte without the need of exchanging- and/or the existence of solutions. This is not the case in the method according to Rappaz et al. In addition, the required laboratory skill of the user is reduced dramatically by removing the process of exchanging solutions and also the risk of contamination of the sample due to user mismanagement. Further, the lack of need to exchange solutions reduces the time for determining said parameters because the method according to the present invention requires only one detection of the interference pattern and reconstruction of amplitude- and phase information representative of said at least one erythrocyte in order to determine said parameters. The method of the present invention can thereby study phenomena's at a very fast rate, wherein the rate is mainly determined by the acquisition rate of the digital detector, detecting the interference pattern.

According to the present invention, both the amplitude- and phase information is used. As such it is possible directly from one image to decide the thickness in each pixel and hence refractive index. As the refractive index should only be dependent on the hemoglobin, it is according to the present invention possible to determine the desired parameters from the blood, such as the mean corpuscular volume, mean corpuscular hemoglobin concentration, oxygen saturation or mean corpuscular hemoglobin of an erythrocyte, Therefore, according to one specific embodiment of the present invention, the combining of phase information and amplitude information representative of said at least one erythrocyte involves determining the refractive index of a sample containing the at least one erythrocyte. According to yet another embodiment, the method is performed by the creation of only one image for the determination of said parameters. This is further discussed below.

In addition, the method of the present invention removes the need for a one time observation vessel and the need for the erythrocytes to adhere to said observation vessel. Further, the artifacts arising due to erythrocytes possible movement or wash out from the observation vessel when exchanging the solutions is removed in the method according to the present invention because of the single detection requirement. The need for an observation vessel with a very well-defined height and solutions with known refractive index is not existent due to the use of amplitude- and phase information according to the present invention. The method further allows the at least one erythrocyte to be sustained in an in-vivo like environment due to the ability of the method to facilitate fluids in conjunction with the at least one erythrocyte.

According to a second aspect, an apparatus for analyzing a sample comprising at least one erythrocyte based on digital holography is provided. The apparatus comprises: at least one light source arranged to create at least one object beam and at least one reference beam of light, wherein said at least one object beam and said at least one reference beam are mutually coherent; means for exposing said sample to said at least one object beam; means for superposing said at least one object beam that has passed through said sample with said at least one reference beam, thereby creating an interference pattern; a sensor arranged to detect said interference pattern; and a processing unit arranged to reconstruct phase and/or amplitude information of object wave front from said interference pattern representative of said at least one erythrocyte and to determine the mean corpuscular volume and/or mean corpuscular hemoglobin concentration and/or mean corpuscular hemoglobin and/or oxygen saturation from said phase- and amplitude information.

The features and advantages of the first aspect generally apply to the second aspect. Further features and advantages of the invention are disclosed in more detail in the following.

DETAILED DESCRIPTION OF PREFERRED EMBODIMENTS OF THE INVENTION

Figure 1:
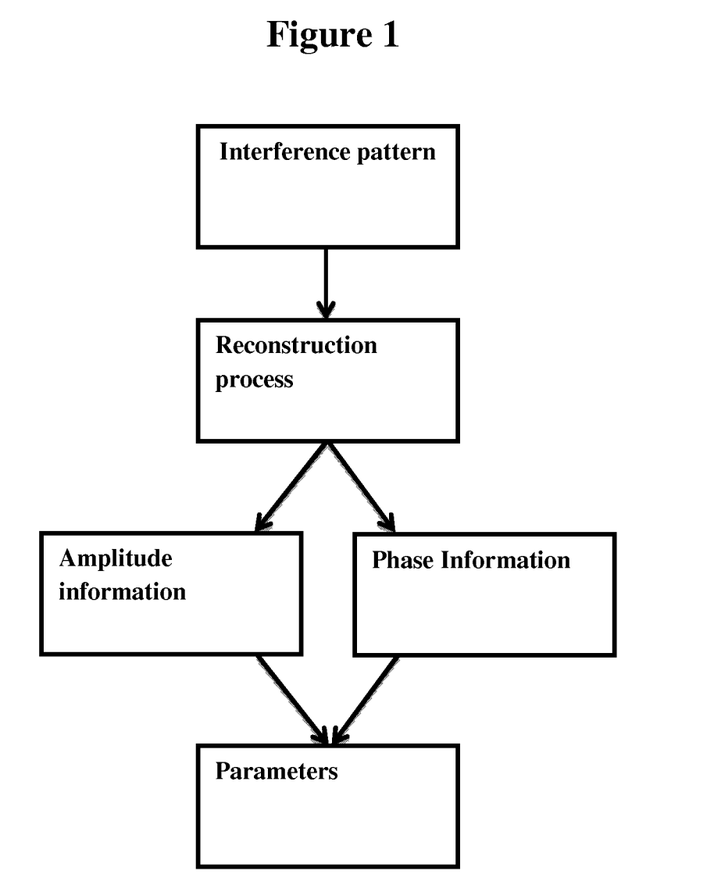
FIG. 1 is a flowchart of the method according to the present invention.

As shown by the flowchart in FIG. 1, a method based on digital holography for determining parameters of at least one erythrocyte is provided, said method comprising the steps of:
constructing an interference pattern comprising a wave front representative of said at least one erythrocyte arised from the interaction of said at least one erythrocyte and electromagnetic radiation;
reconstructing amplitude- and phase information representative of said at least one erythrocyte wave front from said interference pattern; and
determining the mean corpuscular volume and/or mean corpuscular hemoglobin concentration and/or oxygen saturation and/or mean corpuscular hemoglobin of at least one erythrocyte by combining phase information and amplitude information representative of said at least one erythrocyte.

According to one specific embodiment of the method according to the present invention, the electromagnetic radiation has a wavelength in the spectrum of visible light. In other embodiments of the method according to the present invention, electromagnetic radiation in the e.g. infrared- and/or X-ray- and/or ultra violet spectrum may be used. The electromagnetic radiation is generated by a source capable of radiating the at least one wavelength. The electromagnetic radiation source generating radiation in the spectrum of light may be for example any kind of laser source, such as a diode or He—Ne laser. Preferably a diode laser is used.

In one embodiment of the method according to the present invention, the mutually coherent at least one object beam and at least one reference beam of light are created by dividing a light beam originating from a coherent light source into two beams e.g. by means of a beam splitter. The object beam and the reference beam are mutually coherent, meaning that they have the same frequency and exhibit a constant phase relationship during the course of time.

The object beam is passed through the at least one erythrocyte comprised in and/or on an observation vessel adapted to comprise said at least one erythrocyte and capable of allowing radiation of electromagnetic radiation passing through said observation vessel and said at least one erythrocyte comprised in and/or on said observation vessel. The observation vessel is preferably capable of allowing the electromagnetic radiation to pass through the observation vessel with no or minimal influence on the radiation or with a known radiation disturbance effect. The observation vessel may further comprise medium(s) capable of highlighting desired physical characteristics of the at least one erythrocyte, such as morphological changes and/or refractive index changes. The observation vessel may further comprise medium(s) maintaining the at least one erythrocyte in a desired state, such as dead and/or alive and/or growing and/or shrinking with solutions such as, phosphate buffered saline and/or tris buffered saline and/or Hank's buffered salt solution and/or cell growth medium, such as RPMI 1640 with or without supplements.

The reference beam is left unaffected by the at least one erythrocyte comprised in and/or on the observation vessel, since the reference beam is guided along a different optical path than the object beam e.g. by means of mirrors or fiber optics.

Figure 2:
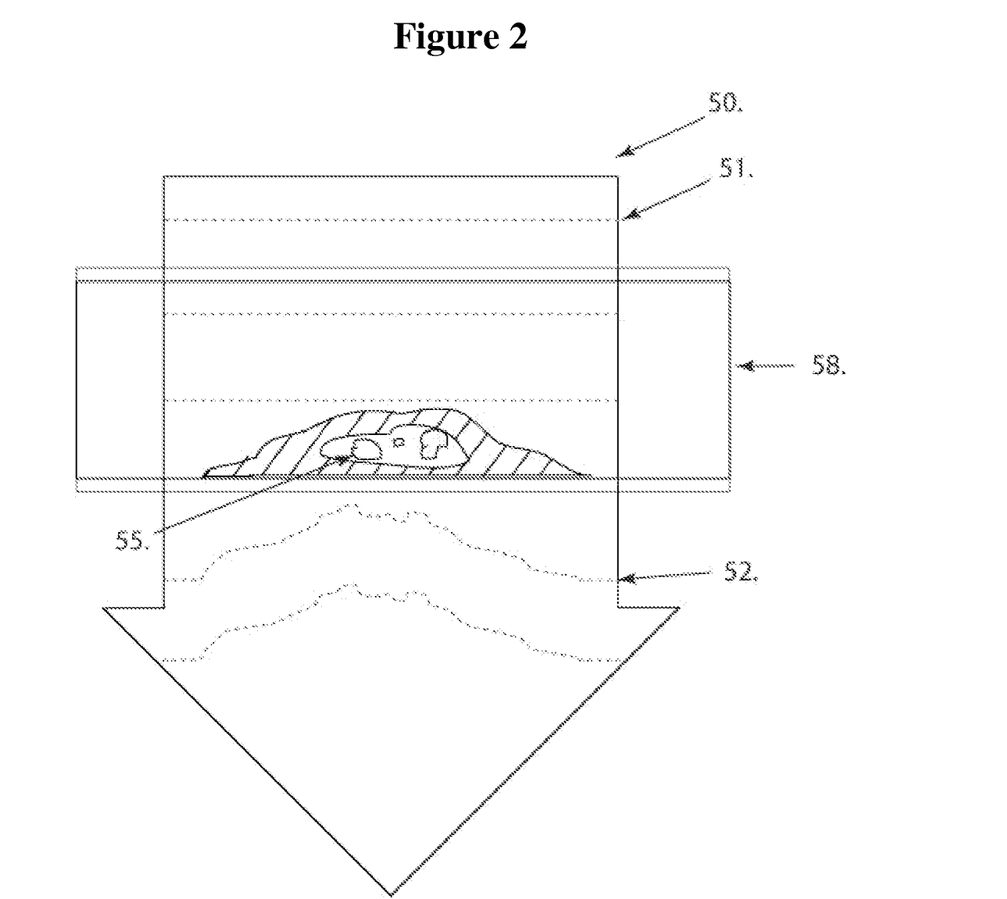
FIG. 2 is a schematic illustration of a wave front of an object beam before and after passage of transparent biological object.

As shown in FIG. 2, the object beam 50 has a known wave front 51 before passing through the at least one erythrocyte 55 comprised in and/or on an observation vessel 58. When the object beam 50 passes through the at least one erythrocyte 55, the at least one erythrocyte 55 will absorb at least a part of the intensity of the object beam 50 and the object beam 50 will experience a difference in optical path length compared to the surroundings because of it passing through the at least one erythrocyte 55. The object wave front 52 that emerges from the interaction between the known object beam wave front 51 and the at least one erythrocyte 55, the object wave front 52, will thus be phase shifted and its amplitude will be affected by the absorption from the at least one erythrocyte 55. In analogy, the reference beam (not shown) also has a known wave front which thus is unaffected by at least one erythrocyte. The optical path is defined as the physical/geometrical thickness multiplied with the refractive index. The absorption is defined as the transformed electromagnetic radiation energy, by the erythrocyte, from wave propagation to other types of energy.

In one embodiment of the method according to the present invention, the superimposing of the at least one object beam that has passed through the at least one erythrocyte comprised in and/or on an observation vessel and the at least one reference beam is achieved by bringing the two beams together e.g. by means of another beam splitter. This interaction of at least one erythrocyte and electromagnetic radiation, superimposition, gives rise to an interference pattern, which comprises information about the object wave front representative of the at least one erythrocyte.

In one embodiment of the method according to the present invention, the interference pattern is detected by means of a digital sensor, such as a charge-coupled device (CCD) or complementary metal-oxide-semiconductor (CMOS). The detected interference pattern is also called a hologram.

To superimpose the at least one object beam that has passed through the at least one erythrocyte and the at least one reference beam and thereby creating an interference pattern and to detect the interference pattern for example a Fraunhofer-, Fourier- or Fresnel setup may be used. Preferably a Fresnel setup is used. The difference between said three setups lays in that the optical configuration fulfills certain conditions allowing for an approximation in the reconstruction of the wave front representative of said at least one erythrocyte. The condition to be met in Fresnel setup allowing for an approximation of the reconstructed wave front, is that the distance between the sensor and the at least one erythrocyte is large compared to the size of the at least one erythrocyte and the size of the sensor. This is achieved by use of a microscope objective that collects the scattered light from said at least one erythrocyte and directs it to the digital sensor in an almost parallel beam, thus creating an optical configuration where the distance between the at least one erythrocyte and digital sensor is large compared to the size of the at least one erythrocyte and the size of the sensor.

From the detected interference pattern amplitude- and phase information of the object wave front is reconstructed. The reconstruction is carried out by means of any common numerical reconstruction process such as Fourier Transform reconstruction and/or Fresnel Transform reconstruction and/or Angular Spectrum reconstruction and/or Convolution reconstruction and/or Wavelet reconstruction. The reconstructed amplitude- and phase information representative of said at least one erythrocyte may for example be represented in each domain, amplitude or phase, as an image and/or map in two dimensions and/or as a 3D representation in three dimension of the at least one erythrocyte information. Preferably the reconstructed information is represented as an image.

The reconstructed information is further used in image processing conducted by a computer in order to determine parameters about the at least one erythrocyte, such as mean corpuscular volume, red blood cell distribution width, mean corpuscular hemoglobin, oxygen saturation and mean corpuscular hemoglobin concentration. Several obtained images may also be further used in image processing in order to determine additional useful information about the studied at least one erythrocyte. Said several images may be taken at different time points and stored for later image processing and or reconstruction, meaning that the method according to the present invention is time independent. Such image processing may involve segmentation algorithms, wherein at least one erythrocyte is located. These located at least one erythrocyte may be further analyzed with respect to morphology, e.g. regarding their width, shape etc. Segmentation algorithms that may be used is watershed segmentation and/or gradient analysis but any type of algorithm for detecting and/or outlining the at least one erythrocyte in an image, may be used. Preferably watershed segmentation is used.

Alternatively, to create one reference beam and one object beam other types of digital holography setups may be used for the generation of interference pattern, for example in-line digital holography where the creation and use of one beam is utilized. It is obvious for a person skilled in the art how to modify the method of the present invention in order to use it in for example in-line digital holography, when studying this specification.

When determining parameters of erythrocytes, such as mean corpuscular volume and/or red blood cell distribution width and/or mean corpuscular hemoglobin and/or oxygen saturation and/or mean corpuscular hemoglobin concentration, the erythrocyte is commonly modeled, from an optical view, as comprising mainly of a homogeneous aqueous solution of hemoglobin, salts and other organic compounds contained in a transparent cell membrane of negligible thickness. The water and the hemoglobin molecules occupy more than 95% of the erythrocyte volume. Therefore, with respect to techniques using forward light scattering e.g. flow cytometers, phase contrast microscopy and digital holography an erythrocyte can be characterized by a volume V and a complex index of refraction $n_c=n_r-n_i$. Since the interior of the erythrocyte is almost completely occupied by water and hemoglobin, variations in refractive index $n_c$, from erythrocyte to erythrocyte can be attributed solely to variations in hemoglobin concentration.

By applying the above described model, Mie scattering theory is applicable and the object wave front comprised in the arised interference pattern from interaction of electromagnetic radiation and the at least one erythrocyte can be detected by a digital sensor. This, results in the possibility to determine said parameters associated with erythrocytes when reconstructing said object wave front representative of the at least one erythrocyte. A problem with this commonly used model of erythrocytes and use in Mie scattering theory, is that the reconstructed wave front depends on two unknown parameters volume V, and the complex index of refraction $n_c$ and additional known parameters. Meaning that the, one, reconstructed wave front comprises two unknown parameters mixed in a non-obvious way.

Figure 3:
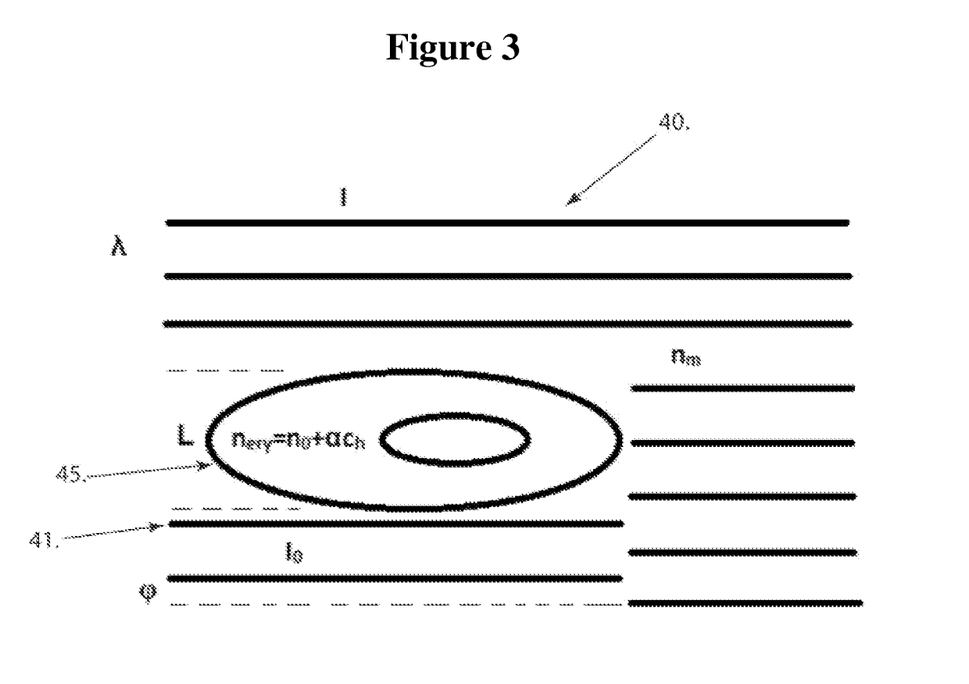
FIG. 3 is an embodiment of the erythrocyte model and conceptual illustration of the method according to the present invention.

In FIG. 3 a conceptual schematic of the method according to the present invention is shown. It will as followed be described, for simplicity, in relation to one erythrocyte but the method according to the present invention is however not restricted to one but preferably to at least one erythrocyte. The wave front 40, is known before it passes through the at least one erythrocyte 45, as also shown in FIG. 2 (51, 55). After at least a part of the known wave front 41, object wave front, have passed through said at least one erythrocyte 45, it will be phase shifted ($\phi$) due to its difference in optical path, $n_{ery} \cdot l$, compared to the at least a part of the wave front 40 that does not pass through the at least one erythrocyte 45, $n_m \cdot l$. The object wave front 41 will also be affected by absorption, Io, from the at least one erythrocyte compared to the known wave front 40, I.

Below, one possible route for determining parameters of interest for the present invention will be described.

In an embodiment according to the method of the present invention, an erythrocytes refractive index is modeled as:

$$n_{ery} = n_0 + \alpha c_h \quad (1)$$

where $n_0$ is the refractive index of an erythrocyte in the absence of hemoglobin, a is the refractive index increment of hemoglobin at a specific wavelength and $c_h$ is the hemoglobin concentration. Further, Beer-Lambert's law states that electromagnetic radiation transmission (A), of a mixture of an absorbing liquid and a non-absorbing liquid is proportional to the concentration (c) of the absorbing liquid and the distance (l) said electromagnetic radiation has travelled through said absorbing liquid:

$$A = -\log_{10}\frac{I}{I_0} = \log_{10}I_0 - \log_{10}I = \epsilon c l \quad (2)$$

where $\epsilon$ is the molar absorptivity of said absorbing liquid, I is the intensity of transmitted light from said mixture and $I_0$ is the intensity of incident light on said mixture.

Assuming that the hemoglobin concentration is constant within an erythrocyte, and/or at least constant during the detection by a digital sensor of the interference pattern comprising the wave front representative of the at least one erythrocyte and as absorption is only caused by hemoglobin, the total absorption of an erythrocyte ($\Omega$), comprised in the wave front representative of said erythrocyte further comprised in the interference pattern and detected by a digital sensor and reconstructed in to amplitude information represented as for example as an amplitude image, is written as:

$$\Omega = \sum_i^{N_p} A_i = \epsilon_h c_h \sum_i^{N_p} l_i \quad (3)$$

where $N_p$ is the total number of pixels representing said erythrocyte in said reconstructed amplitude image, $\epsilon_h$ is the molar absorptivity of hemoglobin at wavelength, $\lambda$, $c_h$ is the hemoglobin concentration and $l_i$ is the thickness of said erythrocyte at pixel i.

As stated above this model depends on the wavelength and can be used at an isosbestic wavelength, meaning a wavelength such as, 525-575 nm, where the molar absorptivity of hemoglobin ($\epsilon_h$) is not dependent on the saturation level of hemoglobin. Alternatively or additionally, when using a wavelength where the molar absorptivity $\epsilon_h$ is dependent on the saturation of the hemoglobin and thus the erythrocyte, the total absorption is modeled as:

$$\Omega = S\epsilon_\lambda^0 c_h \sum_i^{N_p} l_i + (1-S)\epsilon_\lambda^d c_h \sum_i^{N_p} l_i \quad (4)$$

where $\epsilon_\lambda^0$ is the molar absorptivity of oxyhemoglobin at wavelength $\lambda$, S is hemoglobin oxygen saturation and $\epsilon_\lambda^d$ is the molar absorptivity of deoxyhemoglobin at wavelength $\lambda$.

By using equation (1), the relative phase shift ($\phi_i$) at pixel i, comprised in the interference pattern and detected by a digital sensor and reconstructed in to phase information represented as a phase image, is expressed as:

$$\varphi_i = \frac{2\pi}{\lambda}(n_{ery} - n_m)l_i = \frac{2\pi}{\lambda}(n_0 \alpha c_h - n_m)l_i \quad (5)$$

where $n_m$ is the refractive index of the non-erythrocyte surrounding fluid at pixel i. The total phase shift of an erythrocyte ($\Phi$) is written as:

$$\Phi = \sum_i^{N_p} \varphi_i = \frac{2\pi(n_0 + \alpha c_h - n_m)}{\lambda}\sum_i^{N_p} l_i = \frac{2\pi(n_0 - n_m)}{a\lambda}*V + \frac{2\pi\alpha c_h}{\lambda}\sum_i^{N_p} l_i \quad (6)$$

where a is the area imaged by a pixel i and $V = a\sum_i^{N_p} l_i$ is the erythrocytes volume. By using the total absorption of hemoglobin according to equation (3) and the total phase shift according to equation (5), the total phase shift of at least one erythrocyte is alternatively written as:

$$\Phi = \frac{2\pi(n_0 - n_m)}{a\lambda}V + \frac{2\pi\alpha}{\lambda\varepsilon_h}\Omega \quad (7)$$

By rearranging the terms, the volume of at least one erythrocyte is thus expressed as:

$$V = \frac{a\lambda}{2\pi(n_0 - n_m)}\Phi - \frac{a\alpha}{(n_0 - n_m)\varepsilon_h}\Omega \quad (8)$$

It is realized that with the above method according to the present invention the combination of the phase shift and the absorption of the at least one erythrocyte, the mean corpuscular volume, MCV, can be determined by:

$$MCV = \frac{a}{N_{rbc}(n_0 - n_m)} \left[ \frac{\lambda}{2\pi} \Phi - \frac{\alpha}{\varepsilon_h} \Omega \right] \quad (9)$$

where $N_{rbc}$ is the total number of erythrocytes.

Further, the phase shift in a pixel can be expressed by combining equation (2) and (5) as:

$$\varphi_i = \frac{2\pi}{\lambda} \left[ (n_0 - n_m) l_i + \frac{\alpha A_i}{\varepsilon_h} \right] \quad (10)$$

Solving this for pixel thickness gives:

$$l_i = \frac{\frac{\varphi_i \lambda}{2\pi} - \frac{\alpha A_i}{\varepsilon_h}}{n_0 - n_m} \quad (11)$$

Re-inserting this in equation (2) and solving for hemoglobin concentration in a pixel gives:

$$c_{h_i} = \frac{n_0 - n_m}{\frac{\varepsilon_h \varphi_i \lambda}{2\pi A_i} - \alpha} \quad (12)$$

The mean corpuscular hemoglobin concentration (MCHC) can thus be calculated as:

$$MCHC = \frac{1}{N_p} \sum_i^{N_p} c_{h_i} = \frac{n_0 - n_m}{N_p} \sum_i^{N_p} \frac{1}{\frac{\varepsilon_h \varphi_i \lambda}{2\pi (\log_{10} I_0 - \log_{10} I_i)} - \alpha} \quad (13)$$

where $N_p$ is the total number of erythrocyte pixels.

Further, by use of the total absorption in equation 3 and 4 and the definition of the erythrocytes volume in equation 6, the oxygen saturation of an erythrocyte is written as:

$$S = \left[ \left( \frac{\Omega_\lambda}{\Omega_{\lambda i}} \right) \varepsilon_{\lambda i} - \varepsilon_\lambda^d \right] / (\varepsilon_\lambda^o - \varepsilon_\lambda^d) \quad (14)$$

(13) where $\lambda_i$ is the isosbestic wavelength. This implies that the oxygen saturation can be determined by reconstructing amplitude- and/or phase information at two wavelengths, namely the isosbestic and non-isosbestic wavelength. Alternatively, the oxygen saturation can be determined by use of equation 4 at two wavelengths where none of the wavelengths are at an isosbestic wavelength. The oxygen saturation is then written as:

$$S = \frac{\varepsilon_{\lambda 1}^d - \varepsilon_{\lambda 2}^d (\Omega_{\lambda 1} / \Omega_{\lambda 2})}{(\varepsilon_{\lambda 2}^o - \varepsilon_{\lambda 2}^d)(\Omega_{\lambda 1} / \Omega_{\lambda 2}) - (\varepsilon_{\lambda 1}^o - \varepsilon_{\lambda 1}^d)} \quad (15)$$

where $\epsilon_{\lambda 1}^d, \epsilon_{\lambda 1}^o$ is the molar absorptivity of the deoxy- and oxyhemoglobin at a first wavelength and $\epsilon_{\lambda 2}^d, \epsilon_{\lambda 2}^o$ is the molar absorptivity of the deoxy- and oxyhemoglobin at a second wavelength.

Additionally or alternatively, the mean corpuscular hemoglobin, MCH, is determined by:

$$MCH = MCV \cdot MCHC \quad (16)$$

Additionally or alternatively, the red blood cell distribution width, RDW, can be determined by any common edge detection algorithm applied on the reconstructed amplitude- and/or phase image(s) to determine the width of the erythrocytes and thus determine the variation of red blood cell width.

In relation to the present invention it should be noted that the above described route for determining e.g. MCH and/or MCHC constitutes only one example according to the present invention. There exist alternative derivations possible to perform for obtaining the parameters of interest according to the present invention. For example, MCHC may be obtained by first calculating the average concentration for each blood cell and then use the average value of all of the derived average concentrations. Once again, this is also only one example possible according to the present invention, however other routes, derivations and/or equations may also be possible to use according to the invention.

Figure 4:
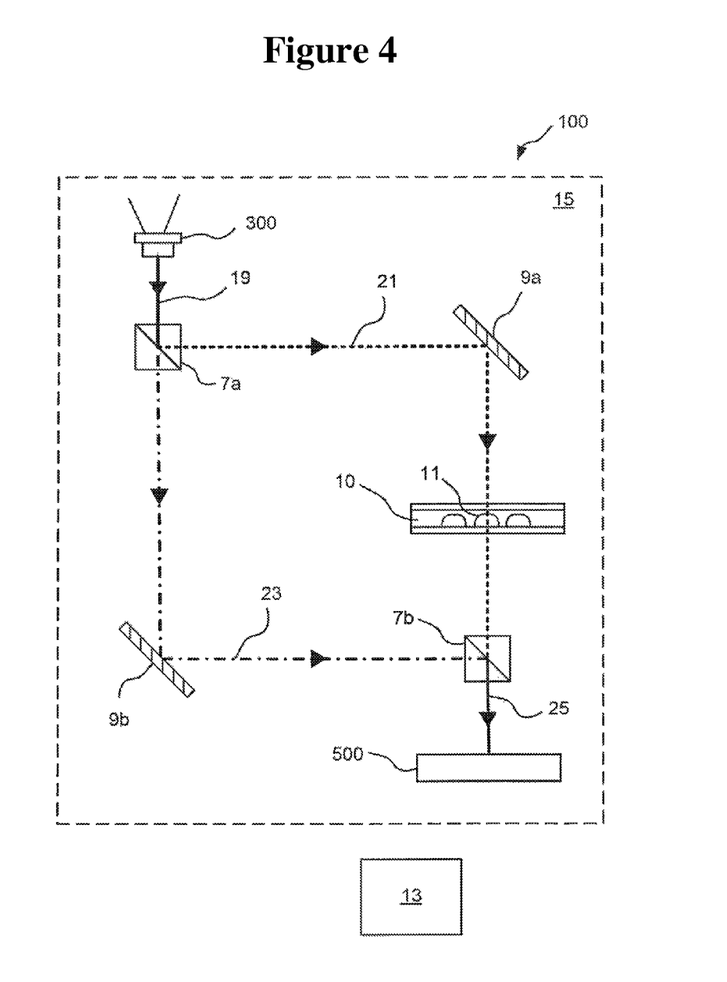
FIG. 4 is a schematic illustration of an apparatus according to an embodiment of the present invention.

An apparatus according to an embodiment of the invention will now be described with reference to FIG. 4. FIG. 4 is a schematic illustration of an apparatus 100 for analyzing a sample 10. The apparatus 100 comprises at least one light source 300, a sensor 500, beam splitters 7a and 7b, reflecting surfaces 9a and 9b, and a processing unit 13. The beam splitters 7a and 7b, together with the reflecting surfaces 9a and 9b, act as means for exposing the sample to at least one object beam 21 and means for superposing the at least one object beam 21 with at least one reference beam 23.

The light source 300 is arranged to create at least one beam 19 of coherent light. The beam 19 of coherent light may for example be a laser beam which originates from any kind of laser source, such as a diode laser emitting light at a wavelength of 635 nm. Here, only one light source is illustrated. In general, however, the apparatus 100 may comprise several light sources 300 which may be used simultaneously. Preferably, if several light sources 300 are used, these create light of different wavelengths. This may be advantageous since the sample 10 reacts differently to light of different wavelengths. Hence more information about the sample may be obtained by using a plurality of light sources 300 having different wavelengths. The beam 19 of coherent light originating from the light source 300 is directed towards a beam splitter 7a. The beam splitter 7a divides the at least one beam 19 of coherent light into at least one object beam 21 and at least one reference beam 23.

With this construction, the at least one object beam 21 and the at least one reference beam 23 become mutually coherent, implying that they have the same frequency and exhibit a constant phase relationship during the course of time. In case more than one light source 300 is present, the beam splitter 7a may divide each of the beams 19 originating from the light sources 300 into a mutually coherent object beam 21 and a reference beam 23. When the apparatus 100 is in use, a sample 10 comprising at least one erythrocyte 11 is arranged in the light path of the at least one object beam 21. For example, the reflecting surface 9a may be used to redirect the at least one object beam 21 such that the sample 10 is exposed to the at least one object beam 21.

As the object beam 21 incides towards the sample 10, the object beam 21 will pass through the sample 10 and, in particular, through the at least one erythrocyte 11. Since the object beam 21 passes through the sample 10, there is a difference in optical path and intensity compared to a beam, such as the reference beam 23, which does not pass through the sample, due to differences in refractive index and absorption. This will in turn lead to a phase shift and amplitude difference between the object beam 21 and the reference beam 23. The optical path length is defined as the physical/geometrical thickness multiplied with the refractive index and the absorption is defined as the transformed electromagnetic radiation energy from wave propagation to other types of energy. The reflecting surface 9b may be arranged to reflect and thereby redirect the at least one reference beam 23. Specifically, the reflecting surfaces 9a and 9b may be arranged such that the at least one object beam 21 and the at least one reference beam 23 are directed towards a means for superposing, here in the form of beam splitter 7b.

The beam splitter 7b superposes the at least one object beam 21 and the at least one reference beam 23 and directs the superposed beam 25 towards the sensor 500. The sensor 500 is arranged to detect an interference pattern arising from the object beam 21 and the reference beam 23. As the object beam 21 and the reference beam 23 are mutually coherent, they will generate an interference pattern at the sensor 500. In particular, since the at least one object beam 21 and the at least one reference beam 23 have traveled different optical path lengths and have different intensities due to the passage of the at least one object beam 21 through the sample 10, the interference pattern is indicative of the phase shift and intensity between the object beam 21 and the reference beam 23.

The sensor 500 may for example be a digital sensor such as a CCD (Charge Coupled Device) or a CMOS (Complementary Metal Oxide Semiconductor) image sensor. The sensor 500 may further be operatively connected to the processing unit 13 which may comprise software and/or hardware for carrying out any common reconstruction process. The reconstruction process may reconstruct phase and/or amplitude information from the interference pattern detected by the sensor 500. The reconstructed information may for example be used to obtain at least one image of the studied at least one erythrocyte 11. The information may for example also be used to determine morphological parameters of the at least one erythrocyte 11. Specifically, the processing unit 13 is arranged to determine parameters, such as MCH, MCV, $S_{O2}$, MCHC and RDW from the phase and/or amplitude information. In other words, the processing unit 13 may be arranged to carry out any data processing steps of the method according to embodiments of the invention. Further, the apparatus 100 may comprise storage media or a memory (not shown). The storage media or memory may be operatively connected to the processing unit 13. Specifically, the storage media or memory may be arranged to store analysis images and time data pertaining to time-points at which changes were detected in the analysis images. The apparatus 100 may be adapted to operate inside an environmental chamber 15. With such an arrangement, the sample 10 does not have to be taken out of the environmental chamber where it is sustained in order to be analyzed. As illustrated in FIG. 4, the light source 300, the sensor 500, and the optical components, such as the beam splitters 7a and 7b and the reflecting surfaces 9a and 9b, are comprised inside of the environmental chamber 15.

The processing unit 13 may either be located inside the environmental chamber 15 or outside of the environmental chamber 15. In case the processing unit is located outside of the environmental chamber 15, it is preferred if the processing unit may communicate wirelessly with the sensor 500. For example, the apparatus may comprise a transmitter (not shown) which is arranged to transmit information pertaining to an interference pattern from the sensor 500 to a receiver operatively connected to the processing unit 13. The transmitter may form part of a transceiver which is arranged to transmit signals to as well as receiving signals from the processing unit 13. Alternatively, the apparatus 100 may comprise an environmental chamber 15. In this case, the environmental chamber 15 is preferably formed integrally with the apparatus 100. Such an arrangement offers a very compact and flexible solution. For example, the apparatus 100, including the integrally formed environmental chamber, may be put on a working desk and may be conveniently moved to another location if desired. Advantageously, by having an environmental chamber 15 integrally formed with the apparatus 100, not all the components of the apparatus have to be arranged inside of the environmental chamber. For example, some of the optical components, such as beam splitters 7a and 7b and reflecting surfaces 9a and 9b, which are sensitive to the conditions inside of the environmental chamber, may be arranged outside of the environmental chamber.

In one embodiment only the sample holder holding the sample 10 is located inside of the environmental chamber 15. The apparatus 100 may further comprise a controller (not shown) for controlling at least one of a humidity, a temperature and a carbon dioxide percentage inside of the environmental chamber 15. In this way, optimal conditions for the at least one erythrocyte may be achieved. Erythrocytes need certain tightly regulated parameters. First of all, the medium needs to hold a pH of 7.4. As media most often are buffered with carbonate, this is most often achieved by supplying 5%-10% $CO_2$ into the atmosphere, although an organic buffer such as HEPES can be used instead. In order to hinder the evaporation of the medium, the atmosphere should be water-saturated. For example, the humidity may be about or above 90-95%. Erythrocyte is preferably sustained at 37 degrees C., although this is cell species dependent. E.g. most mammalian cells prefer 37 degrees C., insect cells prefer 20 degrees C., while avian cells prefer 40-42 degrees C. Further, different strategies may be used in order for the apparatus 100, and in particular the optical components of the apparatus 100, such as the beam splitters 7a and 7b and the reflecting surfaces 9a and 9b, to cope with the conditions inside of the environmental chamber 15.

According to one strategy, the apparatus 100 is arranged inside of the environmental chamber 15 while the temperature inside of the incubator is essentially equal to room temperature. Then, the temperature inside of the environmental chamber is increased at a low rate. In this way, condensation at the optical components of the apparatus 100 may be avoided since there will be no temperature difference between the optical components and the air inside of the environmental chamber 15. According to another strategy, the optical components, such as beam splitters 7a and 7b and reflecting surfaces 9a and 9b may be arranged and/or treated to be able to cope with the conditions inside of the environmental chamber 15. Specifically, the optical components may be treated to avoid condensation. In this way, the apparatus 100 may be arranged inside of the environmental chamber 15 when the temperature inside of the environmental chamber 15 is not essentially equal to room temperature. As a result, the above procedure of slowly increasing the temperature may be avoided.

Although, the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims does not imply that a combination of features is not feasible and/or advantageous. In addition, singular references do not exclude a plurality. Thus, references to "a", "an", "first", "second" etc. do not preclude a plurality.

The invention claimed is:

1. A method based on digital holography for determining parameters of at least one erythrocyte, the method comprising:
   constructing, via a splitter, an interference pattern, the interference pattern including a wave front representative of said at least one erythrocyte arised from interaction of the at least one erythrocyte and electromagnetic radiation;
   reconstructing, via a processor, amplitude information and phase information representative of the at least one erythrocyte wave front from the interference pattern, and the amplitude information including information on at least an absorptivity of the at least one erythrocyte at a wavelength; and
   determining the parameters of the at least one erythrocyte by combining, via the processor, the amplitude information and the phase information representative of the at least one erythrocyte, the parameters of the at least one erythrocyte including one or more of mean corpuscular volume, mean corpuscular hemoglobin concentration, oxygen saturation, and mean corpuscular hemoglobin of the at least one erythrocyte.

2. The method according to claim 1, wherein the combining of phase information and amplitude information representative of said at least one erythrocyte includes determining the refractive index of a sample containing the at least one erythrocyte.

3. The method according to claim 1, wherein the determining the parameters determines the parameters from only one image generated by combining the amplitude information and the phase information representative of said at least one erythrocyte.

4. The method according to claim 1, wherein the determining the parameters includes determining the mean corpuscular volume by:

$$MCV = \frac{a}{N_{rbc}(n_0 - n_m)} \left[ \frac{\lambda}{2\pi} \Phi - \frac{\alpha}{\varepsilon_h} \Omega \right]$$

wherein
   MCV is the mean corpuscular volume, a is a refractive index of the at least one erythrocyte, $\epsilon_h$ is a molar absorption of hemoglobin at a wavelength $\lambda$, $\Phi$ is a total phase shift of the at least erythrocyte, $n_m$ is a refractive index of a non-erythrocyte surrounding fluid, $N_{rbc}$ is a total number of the at least one erythrocyte.

5. The method according to claim 1, wherein the determining the parameters includes determining the mean corpuscular hemoglobin concentration by:

$$MCHC = \frac{1}{N_p} \sum_{i}^{N_p} C_{h_i} = \frac{n_0 - n_m}{N_p} \sum_{i}^{N_p} \frac{1}{\frac{\varepsilon_h \varphi_i \lambda}{2\pi(\log_{10} I_O - \log_{10} I_i)} - \alpha}$$

wherein the MCHC is the mean corpuscular hemoglobin concentration, Np is a total number of the at least one erythrocyte pixels i, $\alpha$ is a refractive index of the at least one erythrocyte, $n_m$ is a refractive index of a non-erythrocyte surrounding fluid, $c_h$ is a hemoglobin concentration, and $\epsilon_h$ is a molar absorption of hemoglobin at a wavelength $\lambda$.

6. The method according to claim 1, wherein the determining the parameters includes determining the mean corpuscular hemoglobin by:

MCH=MCV·MCHC wherein MCH is the mean corpuscular hemoglobin, MCV is the mean corpuscular volume is the MCHC is the mean corpuscular hemoglobin concentration.

7. The method according to claim 1, wherein the determining the parameters includes determining the oxygen saturation by:

$$S = \left[ \left( \frac{\Omega_\lambda}{\Omega_{\lambda i}} \right) \varepsilon_{\lambda i} - \varepsilon_\lambda^d \right] / (\varepsilon_\lambda^o - \varepsilon_\lambda^d),$$

wherein S is the oxygen saturation, $\epsilon_{\lambda 1}{}^d, \epsilon_{\lambda 1}{}^o$ is the molar absorptivity of a deoxy and oxyhemoglobin at a first wavelength $\lambda_1$ and $\epsilon_{\lambda 2}{}^d, \epsilon_{\lambda 2}{}^o$ is the molar absorptivity of a deoxy and oxyhemoglobin at a second wavelength $\lambda_2$, respectively.

8. The method according to claim 1, wherein the determining the parameters includes determining the oxygen saturation by,
   collecting the amplitude information and the phase information representative of at least one erythrocyte from at least two wavelengths, and
   determining the oxygen saturation based on the amplitude information and the phase information representative of at least one erythrocyte from at least two wavelengths.

9. The method according to claim 1, wherein
   the determining the parameters includes determining the oxygen saturation (S) by:

$$S = \frac{\varepsilon_{\lambda 1}^d - \varepsilon_{\lambda 2}^d (\Omega_{\lambda 1} / \Omega_{\lambda 2})}{(\varepsilon_{\lambda 2}^o - \varepsilon_{\lambda 2}^d)(\Omega_{\lambda 1} / \Omega_{\lambda 2}) - (\varepsilon_{\lambda 1}^o - \varepsilon_{\lambda 1}^d)},$$

wherein S is the oxygen saturation, $\epsilon_{\lambda 1}{}^d, \epsilon_{\lambda 1}{}^o$ is the molar absorptivity of a deoxy and oxyhemoglobin at a first wavelength $\lambda_1$ and $\epsilon_{\lambda 2}{}^d, \epsilon_{\lambda 2}{}^o$ is the molar absorptivity of a deoxy and oxyhemoglobin at a second wavelength $\lambda_2$, respectively.

10. The method according to claim 1, wherein said electromagnetic radiation has a wavelength in a visible light spectrum.

11. An apparatus for analyzing a sample by digital holography, the sample including at least one erythrocyte, the apparatus comprising:
   at least one light source configured to create at least one object beam of light and at least one reference beam of light that are mutually coherent such that the generated at least one object beam and the at least one reference beam have a same frequency and exhibit a constant phase relationship;
   at least one reflector configured to direct the at least one object beam through the sample to generate at least one offset object beam;

a splitter configured to superimpose the at least one offset object beam that has passed through said sample with said at least one reference beam, thereby creating an interference pattern representative of the at least one erythrocyte;

a sensor configured to detect the interference pattern; and a processor configured to, reconstruct phase information and amplitude information of an object wave front from said interference pattern, the phase information and the amplitude information representative of said at least one erythrocyte such that the amplitude information includes information on at least an absorptivity of the at least one erythrocyte at a wavelength, and determine parameters of the at least one erythrocyte from the phase information and the amplitude information, the parameters of the at least one erythrocyte including one or more of mean corpuscular volume, mean corpuscular hemoglobin, oxygen saturation, and mean corpuscular hemoglobin concentration.

12. The apparatus according to claim 11, wherein the processor is configured to determine red blood cell distribution.

13. The apparatus according to claim 11, wherein the processor is configured to determine the oxygen saturation by, reconstructing the phase information and the amplitude information representative of at least one erythrocyte at at least two wavelengths.

14. The apparatus according to claim 13, wherein at least two wavelengths are used.

15. The apparatus according to claim 11, further comprising:

an environmental chamber configured to have arranged therein at least one of the light source, the at least one reflector, the splitter, and the sensor.

16. The apparatus according to claim 11, wherein the processor is outside of the environmental chamber, and wherein the apparatus further comprises:

a transmitter configured to transmit the interference pattern from the sensor to the processor.

17. The apparatus according to claim 11, further comprising:

a controller configured to control at least one of a humidity, a temperature and a carbon dioxide percentage inside of the environmental chamber.

* * * * *